United States Patent [19]

Gorman

[11] Patent Number: 5,272,318
[45] Date of Patent: Dec. 21, 1993

[54] ELECTRONICALLY READABLE MEDICAL LOCKING SYSTEM

[75] Inventor: John G. Gorman, New York, N.Y.

[73] Assignee: Novatek Medical Inc.

[21] Appl. No.: 793,460

[22] Filed: Nov. 18, 1991

[51] Int. Cl.5 ............................................. G06K 5/00
[52] U.S. Cl. .................................................. 235/375
[58] Field of Search ............... 235/375, 382, 383, 385, 235/462, 472

[56] References Cited

U.S. PATENT DOCUMENTS

| | | | |
|---|---|---|---|
| D. 297,939 | 10/1988 | Bradbury et al. | D14/116 |
| 4,265,101 | 5/1981 | Kaplan | 70/312 |
| 4,415,802 | 11/1983 | Long | 235/382 |
| 4,476,381 | 10/1984 | Rubin | 235/375 |
| 4,628,193 | 12/1986 | Blum | 235/375 |
| 4,678,894 | 7/1987 | Shafer | 235/375 |
| 4,787,222 | 11/1988 | Irazoqui et al. | 70/57 |
| 4,814,759 | 3/1989 | Gombrich et al. | 340/771 |
| 4,818,850 | 4/1989 | Gombrich et al. | 235/494 |
| 4,835,372 | 5/1989 | Gombrich et al. | 235/375 |
| 4,850,009 | 7/1989 | Zook et al. | 379/96 |
| 4,853,521 | 8/1989 | Claeys et al. | 235/375 |
| 4,857,713 | 8/1989 | Brown | 235/375 |
| 4,857,716 | 8/1989 | Gombrich et al. | 235/462 |
| 4,916,441 | 4/1990 | Gombrich | 235/380 |

FOREIGN PATENT DOCUMENTS

| | | |
|---|---|---|
| 1187585 | 5/1985 | Canada . |
| WO87/00659 | 1/1987 | PCT Int'l Appl. . |
| 1419622 | 3/1972 | United Kingdom . |

*Primary Examiner*—Edward P. Westin
*Assistant Examiner*—John R. Lee
*Attorney, Agent, or Firm*—Jones, Day, Reavis and Pogue

[57] ABSTRACT

A system which requires scanning of identification means associated with a patient and a proposed treatment in order to determine a code necessary to open or render operational a treatment means is disclosed. Because the necessary code is only displayed if the patient and treatment means have been scanned and the information has been audited to verify that it is correct and complete and has been automatically recorded in the scanner's memory, the system ensures that a record of the transaction is made and that only the proper patient is given a particular treatment.

8 Claims, 1 Drawing Sheet

ELECTRONICALLY READABLE MEDICAL LOCKING SYSTEM

BACKGROUND OF THE INVENTION a) Field of the Invention

This invention relates to a lock which serves as a physical barrier which can prevent a treatment from being administered to a patient or a test being conducted until all necessary recordkeeping has been completed. The combination necessary to open the lock—and thus allow the treatment to be administered or test to be performed—can be determined only if medical personnel properly follow a protocol using a bar code reader which ensures that the patient to whom the item is to be administered is the correct patient and that a complete record of the transaction has been recorded.

b) State of the Art

A chronic problem in hospitals is the failure of medical personnel to accurately and completely record each transaction involving a patient. Without complete records, it is impossible to properly allocate and recover costs of each patient transaction. More importantly, without accurate records, it is impossible to know whether a patient has received the correct medications or other treatments at the correct times and in the correct doses. Medical decision making is thus impaired and patient care is compromised.

Various systems have been proposed to correlate a patient with a particular treatment. Moreover, agencies regulating hospitals such as JCAHO require complete and accurate recordkeeping for accreditation. However, all current systems merely address the problem by simplifying the recordkeeping function, while allowing medical personnel to bypass the recordkeeping function. For example, Clinicom markets an electronic bedside charting system known as Clinicare which uses portable hand-held terminals which transmit data to a wall unit via high-frequency radio waves. Patient data are transmitted via telephone lines to the hospital information system mainframe. Personnel, medications, supplies and patients are provided with bar codes. The system can be used to document every aspect of patient care from recording vital signs to controlling medication administration. However, nothing insures that the system is not simply bypassed.

Clinicom has a number of patents relating to its system. For example, U.S. Pat. No. 4,850,009 relates to a portable hand-held terminal with optical means for sensing bar code indicia and having an integrated keyboard, display and electromagnetic transceiver functions. The terminal is capable of wireless interactive communication with a computer system PCT Application No. W087/00659 and U.S. Pat. Nos. 4,835,372 and 4,857,716 describe a system for correlating items with patients using a bar code wand having an LCD display and a key pad. The system provides a cross-check to insure that an identified item corresponds to an identified patient and an audit trail of all transactions relating to patient therapy, including staff ID, date, time, etc. The purposes of the system include reduction of paperwork and increase in recordkeeping accuracy. Nothing insures that it is used.

U.S. Pat. No. 4,814,759 describes a display monitor which is wall-mounted in a patient's room and interacts with a data input device such as the hand-held terminal described in U.S. Pat. No. 4,835,372. U.S. Pat. No. Des. 297,939 is directed to the design of a portable hand-held terminal U.S. Pat. No. 4,818,850 describes bar code labels and methods of attachment to medical items so that nurses can scan the code and thereby record and double check the medication and dosage being administered.

U.S. Pat. No. 4,916,441 describes a portable hand-held terminal for use at patient bedsides to reduce paperwork, improve recordkeeping and increase accuracy of medical treatment.

Each of the foregoing systems is designed to increase recordkeeping accuracy by minimizing the amount of manual data input and simplifying the recordkeeping process. Unfortunately, the systems can simply be bypassed and the treatment administered without using the barcoding system at all and thus do not address the fundamental problem of non-compliance by hospital personnel with the recordkeeping requirement, and there can be no certainty that any safety feature associated with the system's use is ever employed in actual practice by busy hospital personnel. The standard of care desired is that these systems be used 100% of the time. Even a small percentage of treatments given without benefit of the system, i.e., without recordkeeping, is very undesirable. There is a need for a system whose use is not normally bypassed even 1% of the time.

Other devices for correlating patient specimens or medications with the correct patient are similarly deficient in that they can be bypassed and the treatment administered without benefit of their use. For example, U.S. Pat. No. 4,476,381 describes an ultraviolet label on which patient identifying indicia are imprinted. Nothing ensures that the system is used or that the hospital personnel responsible for administration of medications perform the necessary correlation prior to administration. The bar code labeling arrangement of U.K. Patent No. 1,419,622 can likewise be bypassed, as can the sample identification system of U.S. Pat. No. 4,678,894.

Locking systems which prevent opening a medication or blood bag without correlating the item with the proper patient have been proposed as a means to ensure that a treatment is correlated with the proper patient. For example, in U.S. Pat. Nos. 4,265,101 and 4,787,222, manually operated combination locks on a blood bag can only be opened if the patient to whom the blood is to be administered has the correct combination attached to him. Canadian Patent No. 1,1187,585 provides a locking system in which the patient and the treatment container have matching machine and man-readable identification codes. A scanning means, such as a wand reader, reads the two codes and, if the codes match, releasing means open the lock. The operator may create a label recording the information concerning the treatment by manually operating a keyboard. Nothing in this system ensures that the recordkeeping is done, is accurate or is complete.

While these locking systems prevent administration of an improper treatment to a patient, they do not address the recordkeeping problem.

In contrast to these prior art systems, the present invention prevents administration of a treatment until a protocol has been followed in which the patient and the treatment have been correlated and an accurate record of the treatment has been made.

SUMMARY OF THE INVENTION

This invention relates to a medical safety and recordkeeping system which cannot be bypassed comprising:

(a) a machine readable identification means associated with a patient;

(b) a treatment means;

(c) a machine readable identification means for the treatment means, said treatment identification means containing lock code information which is readable only by machine;

(d) locking means for said treatment means;

(e) scanning means for reading the patient and treatment identification means and for visually displaying the lock code information in man-readable form when the patient identification means and the treatment identification means match; and (f) memory means associated with said scanning means for automatically recording information from the patient and treatment identification means, whereby a record of each patient transaction is automatically created.

BRIEF DESCRIPTION OF THE DRAWING

The FIGURE is a block diagram of a preferred embodiment of the invention.

DETAILED DESCRIPTION OF THE INVENTION

Figure 1:
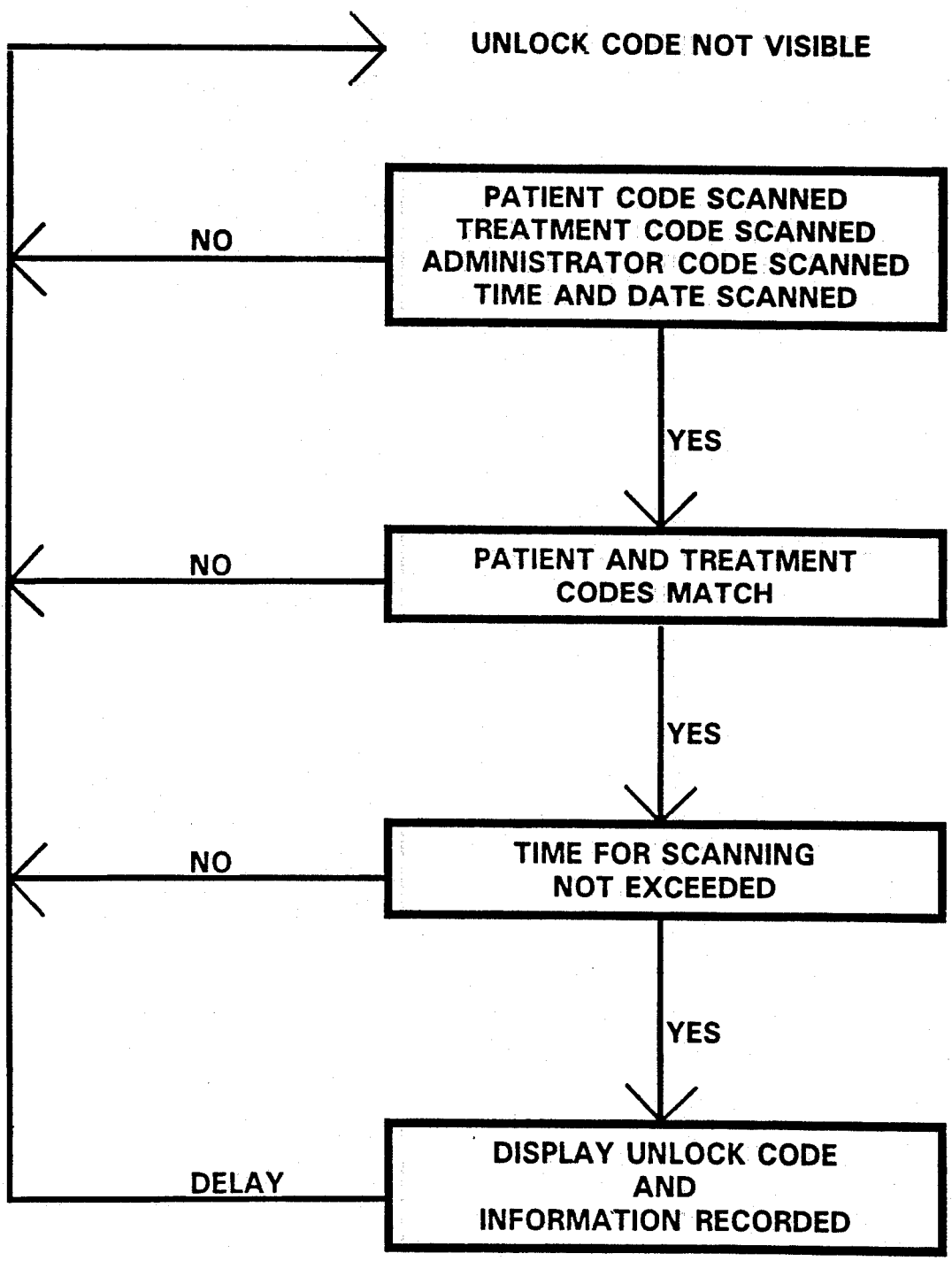

In accordance with the practice of the invention, a patient is given an identification code which is machine readable, preferably by a bar code scanner. Each item to be administered to the patient or with which the patient is to be treated is also provided with a matching machine readable identification code. As used herein, "matching" and "match" mean that the patient identification and the treatment identification in some manner correlate in the scanning device used. For example, they may be the same number or they may be two numbers which the logic and/or memory of the scanning device treat as correlating.

Each treatment or medication is locked and cannot be administered until the lock is opened. Opening the lock can be effected only by scanning the patient identification code and the identification code on a treatment which is to be given to the patient. If the patient identification and treatment identification codes match, the scanner will display in man-readable form the combination or code necessary to open the lock. This display of the combination code may be effected, for example, as a direct result of matching patient/treatment scans or by scanning an additional code on the treatment which reveals the code or combination. In preferred practice, the lock itself will have the code necessary to reveal the code or combination needed to unlock it. This permits having combinations randomly set at the point of manufacture and eliminates the possibility of human error in setting the codes at the time a treatment is locked, and the random selection of combinations at the manufacturing sites reduces the possibility of duplicate codes being chosen by personnel at a single treatment location.

The scanning means has memory means associated with it which automatically records the patient's identity and the treatment which is being administered. Ideally, the system would also require scanning and recording the identity of the individual administering the treatment, as well as recording the time and date of the treatment. This automatic recordkeeping during scanning of the patient and treatment identification codes, in combination with the locking means, ensures that treatments are given only to the correct patients and that a full, accurate record is made each time a treatment is administered.

This invention has application to virtually any treatment which is intended to be administered. For example, blood transfusions and medications can be kept in locked containers which cannot be opened until the code is determined by scanning the patient and container identification codes and getting a proper match. Equipment for treatments can likewise be provided with locks, particularly combination locks requiring punching or dialing alphanumeric characters into the equipment in order to activate the piece of equipment. Even recordation of routine hospital events, such as taking blood pressure and temperatures, can be compelled by preventing use and/or re-use of the equipment until an accurate record has been made of the use. In the context of this application, the term "treatment" is intended to encompass all types of transactions, including the foregoing specifically mentioned transactions involving a patient, but also including transactions involving patient test specimens and/or reagents.

The invention also has application to any process where recordkeeping is mandatory. For example, in certain laboratory situations, it is required that careful records be kept of reagent use. With the present invention, the recordkeeping is guaranteed if a lock prevents opening the reagent without making the necessary record by scanning the reagent. In addition to recordkeeping, it is possible for the present invention to prevent use of expired reagents or other treatments if the scanner is programmed to display the lock code information only if the reagent or treatment is unexpired.

In diagnostic testing, it is particularly important that the reagent used with a test specimen be carefully recorded. If the reagents bear necessary locks and bar codes, the invention will insure that the requisite recordkeeping is done. In such cases, a match between a test specimen identification and the reagent identification will reveal the code for the reagent locking means. Reference to patient identification means in this application is intended to include the identification means used on test specimens from a patient.

The locking means used in the invention may be any barrier means which is opened by use of a code. "Code" as used herein refers to any information necessary to open the locking means which can be determined only if the necessary protocols are followed. For example, codes include combinations for locks, instructions for opening and the like.

Combination locks of the type contemplated in U.S. Pat. Nos. 4,265,101 or 4,787,222 or any other combination lock may be used as the locking means. The degree of uniqueness desired for the particular combination will determine the number of combinations. For example, the locks of the foregoing patents may have few or even one ring if relatively few combinations are necessary. However, the lock should have a sufficient number of combinations such that completing the protocol contemplated in the present invention is considerably simpler than picking the lock. The lock may be as simple as a conventional childproof cap, with the correct open position determined by rotating the cap until a specific alphanumeric character lines up with a specific location on the rim of the container.

Another alternative would be a pull tab which bears an identifying letter or number. A series of dummy tabs would also be present. If the wrong tab is pulled, it would prevent use of the correct tab, for example by breaking it. Alternatively, pulling the wrong tab could have the effect of releasing a reagent (e.g. methylene blue) which would visibly stain the medical personnel's hands. The stain would be a stigma which would give notice to supervisors that the stained individual was not following correct protocols.

The identification codes used may be any scannable code means. Bar codes are preferred and this application will describe the invention in terms of bar codes without intending to limit the invention to such codes.

The patient identification means is preferably a bar code associated with the patient, preferably on a wristband which is not removed until a patient has been discharged. The bar code contains information which conveys the identity of the patient. Preferably, it also conveys other information key to proper treatment of the patient, such as allergies.

Each hospital treatment item also has an identification means, preferably a bar code, which (i) identifies the item, (ii) "matches" patient codes with treatment codes where proper, and (iii) provides, in man-readable form, the code necessary to unlock the item for use. Each of these three identification elements may be discreetly contained on separate bar codes or two or more may be disposed on a single bar code. For example, a manufacturer could apply the item identification and locking information to each dosage unit with the hospital pharmacy applying the patient matching code. Alternatively, the hospital pharmacy or hospital personnel can apply the entire treatment identification means.

The bar code scanner is simply used to scan the patient's identification code and the treatment item's code. Only if the patient's code and the item's code match will the code necessary to unlock the item for use be displayed on the scanner in man-readable form. Preferably, the scanner display will prompt the administrator which of the series of various identification items to read next in order and wait to receive appropriate data. Generally, the scanner will have a computer based algorithm which determines whether all the necessary information has been read and is correct before the combination for the lock is displayed in man-readable form.

The machine readable identification means associated with a patient is usually a unique patient identification number that each patient is issued for life, different however at each hospital he is admitted to. It should be attached to the patient's person, usually imprinted in man-readable form on a wristband. In optimal practice, the machine readable version of this identification number attached to the patient's person is machine distinguishable from the identification number that is attached to the treatment means as its "address."

A machine readable identification number of the treatment itself can be a code that signifies the type of medication or treatment and the dose dispensed in the present item or package. This can be a single code or number, and if so will require electronic consulting of a lookup table of treatments and their unique code identification numbers to obtain a detailed description or specification of just what the medication is. The preferred site for this table is in the memory of a hand held reader so that the full treatment description can be displayed to the administrator when the barcode is read.

Matching codes may be accomplished by simply having each item intended for a particular patient coded with that patient's full identification code with complete identity required for display of the lock code. With items in more common use, where individually labeling each piece of equipment or each dose at the hospital may prove cumbersome, a match might simply require identity of a portion of the patient's and the item's code to display the lock code. For example, over-the-counter medications might simply require that a small portion of each patient's code match the item's code. So long as all patients to whom the item may be administered are given a matching code segment somewhere in their identification bar code, administration of the medication is possible since the lock code can be deciphered. As coding becomes standardized, coding may be done by the pharmaceutical or reagent company when it individually packages units.

Decoding the lock is accomplished by simply scanning the portion of the treatment identification means containing the lock code, preferably using a conventional bar code scanning wand. As previously indicated, only if the scanner detects a match between patient and treatment item—and after all required barcode swipes of patient, treatment address barcode, treatment description barcode, administrator's barcode, automatic time and data obtained from the clock calendar have been performed and the information picked up by them audited and found to be correct and complete, i.e., a legal patient identification number, a legal and matching patient identification number on the treatment, an identification number of a nurse authorized to perform the treatment—will scanning of the lock code result in a visual display of the lock code. The details of each transaction are collected to be saved in memory.

An alternative method of obtaining the combination that the lock was set to is to compute it by a standard and constant mathematical function from the patient identification number. Such a mathematical function will always produce the same combination from the same source patient identification number. This same mathematical function would be used in the pharmacy or blood bank to obtain the combination that the lock is to be set to. In this case, the combination is nowhere present in any of the barcodes, but is computed when needed by microprocessor based programs in a calculator or resident in the scanner itself. This mathematical function could take input from the clock calendar as well as the patient identification number so that a different lock combination would be computed on different days, preventing an obsolete medication dispensed on a previous day or at an earlier hour from being administered.

Because the code is not man-readable until a match is made, only those patients for whom a treatment is intended will receive the treatment. Also, since each dose of an item can have a different locking code, thus preventing memorization of the locking code for an item or a patient, the lock code can be determined only if the scanning steps are completed, even for repeat treatments to a patient.

The scanner is provided with a means for auditing the information obtained by the required barcode scanning of all the various barcode labels and with a means for determining that the information collected is legal and complete. It is preferably also provided with an electronic clock calendar to provide the date and time of day of the treatment. Finally, the scanner has a means for displaying the lock code in man-readable form. The scanner incorporates a microprocessor, computer memory and resident computer programs necessary to support these functions. The scanner has means for recording the information scanned. This information is preferably stored in a computer memory which can be downloaded into the hospital's central computer memory according to conventional means.

In preferred practice, hospital personnel are also provided with bar code identification. Optimally, the lock code cannot be decoded unless the identity of the person administering the treatment is also scanned and recorded. It is also preferred that the scanner be provided with clock means for recording the time and date of each treatment.

Thus, as shown in FIG. 1, in most preferred practice the scanner scans the patient identification means, scans the treatment identification means and scans the hospital personnel identification means, and only upon completion of these three necessary scans and only if a match between the patient and treatment identification means is detected, displays the lock code while recording the information from the scans along with the date and time.

To further ensure accurate administration of treatments and recordkeeping, the scanner may be provided with a timing means which inactivates the display means if the necessary scans do not occur within a set period of time. Thus, if a patient identification means and a treatment identification means are scanned at one bedside, and the nurse takes the time to move to a second bedside before unlocking the treatment, the lock code display will have disappeared and will prevent administration of the treatment to the second patient.

Thus, for example, the display of the code will not appear unless all the required and correct barcodes are read within a few seconds of each other. Thus, if the only location of a patient identification number is on the patient's person and the only location of a medication address barcode or treatment description barcode and the only location of a legal lock combination barcode is on the medication or lock, this timer guarantees that all of these items have to be assembled together at one time and one place, at the patient's side. It is the system's combination of the several kinds of codes with the timer that guarantees the transaction is recorded and monitored right at the correct patient's side after a record has been made.

Because a record is made each time a patient/treatment match is detected, and because it is impossible to administer a treatment without going through the required scans necessary to decode the lock, the invention both compels recordkeeping and insures accurate patient treatment.

In practice of the invention, upon admission to the hospital, a patient will be issued a wristband that contains patient identification information in man-readable form and in machine-readable form. The machine-readable form of patient identification information is preferably bar coded. Other information, such as the date of admission and the name of the attending physician may also be provided on the wristband. At the same time, a number of patient labels bearing patient identification information in machine-readable form may be printed for use at the nursing station to which the patient is assigned. These labels can be used on prescription blanks and diagnostic order forms written for the patient by the attending physician.

When a prescription is written for a patient, a patient label will be applied to the prescription blank and sent to the pharmacy. The prescription may alternatively go to the pharmacy over a computer line and be printed out on a pharmacy printer with the order and patient identification information. When the prescription is filled, the treatment will be placed in a security container which is then locked.

The preferred embodiment of the invention is to have a supply of locks in the pharmacy or blood bank which are preset to random codes by the manufacturer. Each lock has a permanent machine readable barcode label printed by the manufacturer containing the code which will open the lock. There is no man-readable label for this code. One of these preset prebarcoded locks is chosen at random from the supply to lock up the treatment. In this preferred scheme, the code remains unknown to the person dispensing the treatment.

An alternative embodiment is to have a supply of resettable locks in the pharmacy or blood bank. The code is chosen randomly or by the pharmacy computer. The lock is set to this code to lock up the treatment item. The code is encoded in a barcode label printed on the treatment label.

The container is then provided with a treatment label that is printed with machine-readable patient matching identification information, man-readable and machine-readable treatment information and the code for the lock. Information to enable the lock to be unlocked is provided only in machine-readable form preferably on the lock itself or on the medication container label. The machine-readable information is preferably provided as a bar code.

When a nurse brings the treatment secured within its locked container to the patient's bedside, the following procedure is complied with. The nurse uses the bar code scanner with which she is supplied to scan the bar code on the patient's wristband to identify the patient, the patient identification information on the container label which identifies the treatment, and the lock unlocking information on the lock or on the container label. If there is a correlation between the patient identification information on the wristband and on the container label (and if the information collected is determined to be complete and correct by the algorithms resident in the scanning device within the time allowed by the timing means), the scanner will visually display for a short period of time in man-readable form the lock unlocking information scanned on the lock or on the container label. With that information, the nurse will be able to unlock the lock to gain access to the treatment within the container and to administer the treatment to the patient. The patient identification information on the wristband can be differentiated from the same patient identification information on the container label so that the separate bar codes must be read, and not one or the other bar code read twice.

In the preferred system the nurse will also scan her identification information from her identification tag. A record of the time of day and date that the treatment is administered is optimally obtained from clock and calendar means provided in the scanner. Thus, there is a complete record of treatments administered to patients, by whom administered and at what time. This information can later be uploaded to a hospital's central computer when the nurse returns to the nurses, station and plugs the scanner into a terminal located at the station. The information can also be sorted and used to print out individual pages of treatment transactions for each patient to be distributed to each patient's chart.

What is claimed is:

1. A medical safety and recordkeeping system which cannot be bypassed comprising:
   (a) a machine readable identification means associated with a patient;
   (b) a treatment means;
   (c) a machine readable identification means for the treatment means;
   (d) locking means for said treatment means;
   (e) lock code identification means containing information which is readable only by machine;
   (f) scanning means for reading the patient, treatment identification and lock code identification means and for visually displaying the lock code information in man-readable form when the patient identification means and the treatment identification means match; and
   (g) memory means associated with said scanning means for automatically recording information from the patient and treatment identification means, whereby a record of each patient transaction is automatically created.

2. The system of claim 1 wherein the patient identification means is a bar code on a patient's wristband.

3. The system of claim 1 wherein the treatment identification means is a bar code.

4. The system of claim 1 wherein the locking means is a combination lock.

5. The system of claim 1 wherein the scanning means is a bar code scanning wand.

6. The system of claim 1 further comprising administrator identification means which must be scanned before the lock code can be displayed.

7. The system of claim 1 further comprising clock means to provide the time of administration of the treatment which is recorded by the memory means along with the patient identification and treatment information.

8. A medical safety and recordkeeping system which cannot be bypassed comprising:
   (a) a treatment means;
   (b) a machine readable identification means for the treatment means;
   (c) locking means for said treatment means;
   (d) lock code identification means containing information;
   (e) scanning means for reading the treatment identification and lock code identification means and for visually displaying the lock code information in man-readable form; and
   (f) memory means associated with said scanning means for automatically recording information from the treatment identification means, whereby a record of each transaction is automatically created.

* * * * *